US00PP09070P

United States Patent [19]

Button et al.

[11] Patent Number: Plant 9,070

[45] Date of Patent: Mar. 7, 1995

[54] AGLAONEMA PLANT NAMED 'ROYAL RIPPLE'

[75] Inventors: Richard J. Button, Miami; Ann E. Lamb, Lake Placid, both of Fla.

[73] Assignee: Sunshine Foliage World, Zolfo Springs, Fla.

[21] Appl. No.: 223,998

[22] Filed: Apr. 6, 1994

[51] Int. Cl.[6] ..... A01H 5/00

[52] U.S. Cl. ..... Plt./88.1

[58] Field of Search ..... Plt. 88.1

*Primary Examiner*—Howard J. Locker

*Attorney, Agent, or Firm*—Foley & Lardner

[57] ABSTRACT

An Aglaonema plant named 'Royal Ripple' characterized by its wavy tricolor foliage prominently marked with silver-green, rapid growth, and tolerance to cold.

2 Drawing Sheets

The present invention comprises a new and distinct cultivar of Aglaonema, botanically known as *Aglaonema hybrida,* and referred to by the cultivar name 'Royal Ripple'. The new cultivar is a product of a planned breeding program carried out by the inventor Richard J. Button in Miami, Fla., The new cultivar was selected from the progeny of a cross of unknown parentage made by the inventor.

The first act of asexual propagation of 'Royal Ripple' occurred when offshoots and tissue culture of plants of the new cultivar were taken in Palmdale, Fla., under the supervision of Ann E. Lamb. That and subsequent asexual reproduction, both by tissue culture and offshoots, have clearly established that the combination of characteristics of the new cultivar disclosed herein are firmly fixed and are retained through successive generations of asexual reproduction.

The following observations, measurements and values describe plants grown in Zolfo Springs, Fla. under shade house conditions which closely approximate those generally used in horticultural practice.

The following traits have been repeatedly observed to be characteristics which in combination distinguish 'Royal Ripple' from other Aglaonema of the same general type, for example, the well-known cultivar 'Maria', to which 'Royal Ripple' is compared.

1. The leaves of 'Royal Ripple' are larger, wider and distinctly wavy along the margin.

2. The leaves of 'Royal Ripple' are marked with three shades of green, and have considerably more silver-green markings than 'Maria'.

3. The habit of 'Royal Ripple' is more spreading when compared to Maria.

4. Plants of 'Royal Ripple' grow rapidly, attaining marketable size in 10% less time than 'Maria'.

5. Plants of 'Royal Ripple', unlike 'Maria' show little or no foliar damage when exposed to 38° F. for approximately three (3) hours.

All color references are measured against The Royal Horticultural Society Colour Chart. Colors are approximate as color depends on horticultural practices such as light level and fertilization rate, among others, without, however, any variance in genotype.

The drawings comprise a color photograph and a color photocopy of 'Royal Ripple'.

The color photograph comprising sheet 1 is a top perspective view of a plant of 'Royal Ripple' in a 26 cm pot approximately 69 weeks after planting a single four-leaf cutting and grown under appropriate growing conditions.

The color photocopy on sheet 2 illustrates in greater detail the leaf color pattern of the adaxial surface.

Colors are as accurate as possible with color illustrations of this type.

Origin: Seedling selected from a cross of unknown parentage.

Classification: *Aglaonema hybrida,* cv 'Royal Ripple'.

Propagation: Asexual propagation either by division or tissue culture.

Plant: When a four-leaf cutting is grown in a 26 cm pot for approximately 69 weeks under appropriate growing conditions, mature plants of 'Royal Ripple' are approximately 15.0 cm to 17.5 cm in height from the soil surface to the junction of the petioles of the last two (2) unrolled leaves, and approximately 81.0 cm to 89.0 cm in width.

Stem:

*Growth pattern.*—The stem is erect in growth and approximately 1.3 cm to 1.5 cm in diameter five (5) cm above the soil surface. Internode distance is approximately 1.6 cm to 2.2 cm three (3) cm above the soil.

*Color.*—Immature: 146 D. Mature: 146 A-B.

Petiole: The following information is based on the fourth expanded leaf from the apex.

*Growth pattern.*—The petiole has fleshy edges extending from the midrib and referred to as wings. The wings are approximately 5 mm to 7 mm wide one-half the distance from the petiole base to the wing apex. The wings extend from the base of the petiole to within approximately 6.5 cm to 9.6 cm of the base of the leaf. The apex of the wings is unevenly rounded and often torn. The petiole follows the stem axis but diverges from the axis approximately 11.0 cm to 15.5 cm from the leaf base, forming a horizontal distance from the edge of the stem to the leaf base of approximately 6.0 cm to 8.9 cm.

*Dimensions.*—The petiole is straight from its base to approximately the end of the wing, and often curved from approximately the end of the wing to the base of the leaf. The petiole is approximately 7.0 mm in diameter one-half the distance between the top of the wing and the base of the leaf. The petiole is approximately 15.0 cm to 19.5 cm in length.

*Color.*—The petiole color is darker than, but closest to, 147 A, mottled with 147 D. The petiole wings are 147 A-B mottled with 147 D.

Leaf:

*Growth pattern.*—The leaf is ovate with an acuminate apex and a cordate base. The margin is entire. The leaf is asymmetric with the side of the leaf unrolling first having less surface area than the side unrolling last. The leaf is oriented parallel to the stem axis at the time of full unrolling, changing to approximately 50 degrees above perpendicular to the stem axis as more leaves unroll above it. The midrib is straight and the leaf tip is curved downward. The leaf blade is flat from the midrib to the margin. The leaf margins are distinctly wavy.

*Dimensions.*—For the pot size and growing time indicated, the largest leaves are approximately 26.5 cm to 29.0 cm long and approximately 9.0 cm to 10.0 cm wide. Average-sized leaves are approximately 22.0 cm to 25.0 cm long and approximately 7.5 cm to 8.5 cm wide. The leaf is moderately thick.

*Midrib.*—The midrib is thick and prominent, recessed on the adaxial leaf surface and protruding from the abaxial surface. The color of the adaxial leaf midrib on new and mature leaves is darker than, but closest to, 147 A. The abaxial midrib is 147 B, lightly mottled with 147 D on both new and old leaves.

*Primary veins.*—The primary veins are sunken into the upper surface and protrude slightly from the underside. The primary veins are the same color as the surrounding leaf tissue on the adaxial leaf surface. The primary veins on the abaxial leaf surface are 147 A lightly mottled with 147 C.

*Leaf color pattern.*—The adaxial leaf surfaces are marked with three shades of green. Dark green markings are located along the midrib and along the leaf margin. Large, predominant but irregular areas of silver-green, beginning at the midrib and terminating near the leaf margin, mark the entire length of the leaf. There are irregular blotches of a third shade of silver-green which radiate out from the midrib to the leaf margin. Colors: Dark green markings — New leaf is 147 A, mature leaf is darker and greener than, but closest to, 147 A. Predominant silver-green markings — New leaf is 147 B, mature leaf is 147 B-C. Secondary silver green markings — New leaf is 137 B, mature leaf is 137 A-B. The abaxial leaf surfaces are 146 A-B on new and 137 B-C on mature leaves.

*Axillary breaks.*—There are approximately 16 axillary breaks with at least one leaf expanded. Leaves show true color and pattern by the first leaf.

*Inflorescence.*—Typical of Aglaonema and does not have commercial significance.

Roots: Thick white roots with fine laterals.

General observation: Aglaonema 'Royal Ripple' has leaves with wavy margins prominently marked with two shades of silver-green on a dark green background. Plants of 'Royal Ripple' grow rapidly and tolerate temperatures as low as 38° F. for approximately three (3) hours without noticeable foliar damage. These combined characteristics make 'Royal Ripple' a unique new cultivar.

We claim:

1. A new and distinct cultivar of Aglaonema plant named 'Royal Ripple', as illustrated and described.

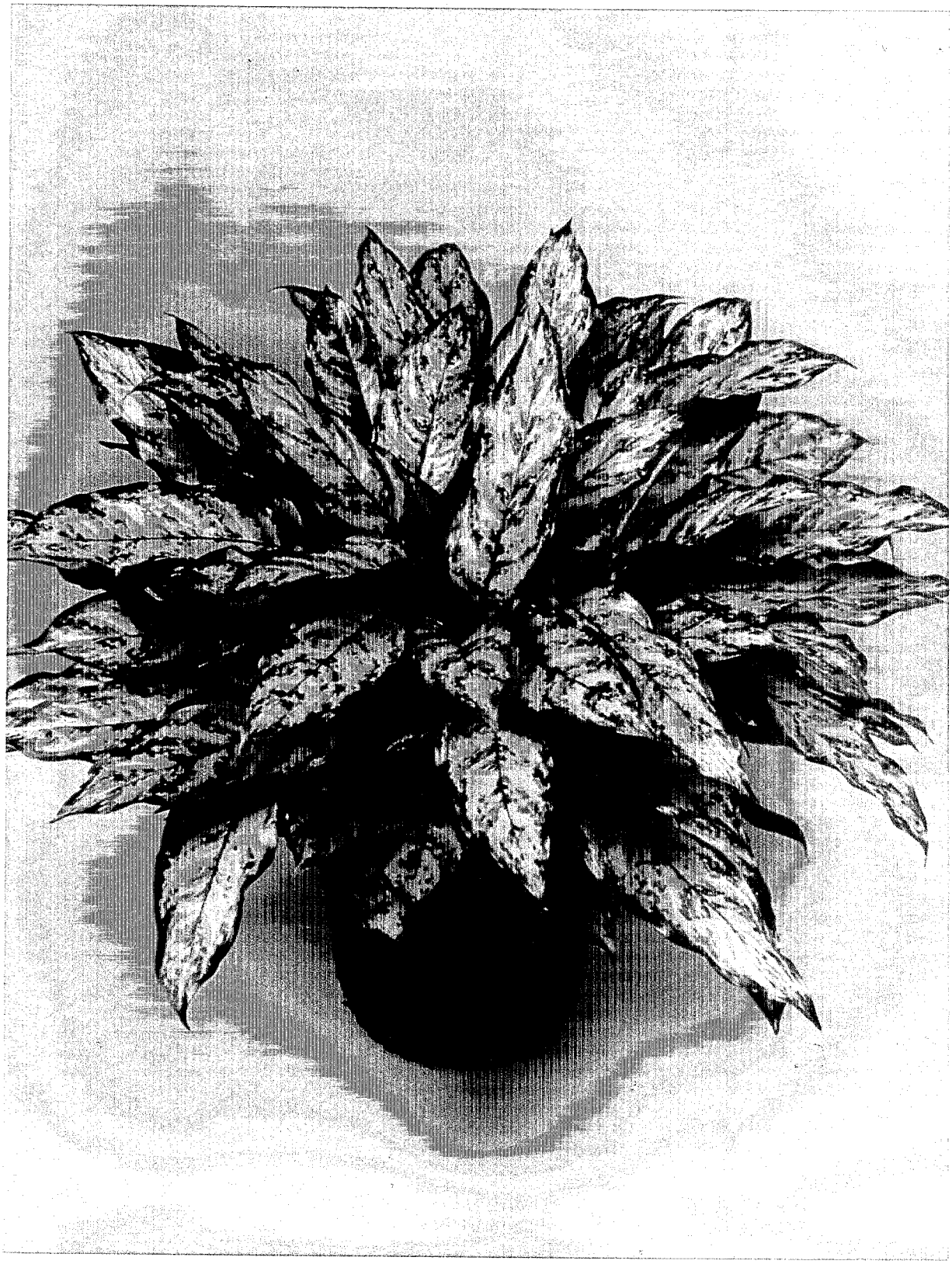

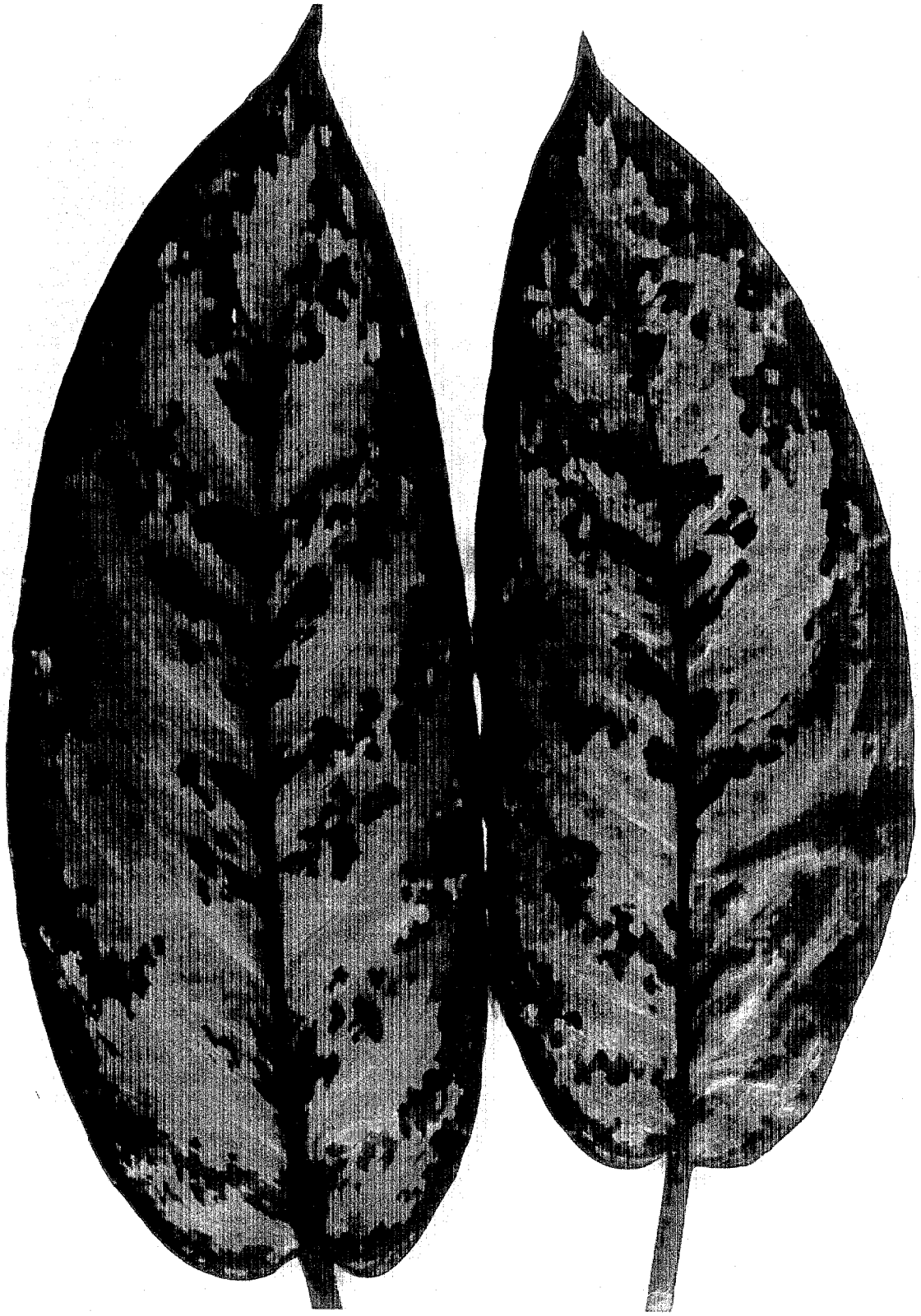

* * * * *